United States Patent [19]

Gejkova et al.

[11] Patent Number: 5,244,673
[45] Date of Patent: Sep. 14, 1993

[54] MEDICAMENTOUS FORM FOR USE AS AN OPHTHALMOLOGIC, OTOLARYNGOLOGIC, OR DERMATOLOGIC DRUG

[75] Inventors: Jitka Gejkova; Jiri Vacik; Zdenek Lojda, all of Praha, Czechoslovakia

[73] Assignee: Institute of Macromolecular Chemistry of the Academy of Sciences of the Czech Republic, Praha, Czechoslovakia

[21] Appl. No.: 588,322

[22] Filed: Sep. 26, 1990

[30] Foreign Application Priority Data

Sep. 29, 1989 [CS] Czechoslovakia .................. 5552-89

[51] Int. Cl.$^5$ ..................... A61K 37/64; A61K 47/34; A61K 47/38
[52] U.S. Cl. ................................ 424/486; 424/94.64; 424/94.67; 424/488; 514/8; 514/12
[58] Field of Search .................. 424/401, 94.64, 94.67, 424/78.04, 486, 488; 514/12, 8

[56] References Cited

U.S. PATENT DOCUMENTS

| | | | |
|---|---|---|---|
| 3,868,445 | 2/1975 | Ryde et al. | 424/78.04 |
| 3,932,618 | 1/1976 | Fujii et al. | 424/94.67 |
| 4,849,406 | 7/1989 | Salonen | 514/8 |

Primary Examiner—Thurman K. Page
Attorney, Agent, or Firm—Notaro & Michalos

[57] ABSTRACT

A medicamentous form or composition with antiexudation, antiphlogistic, and antimicrobial effects in an aqueous or ointment base, suitable above all as an ophthalmologic, otolaryngologic, or dermatologic drug contains inhibitors of proteases such as aprotinin, soybean trypsine inhibitor, and elastatinal either single or in combination. The composition may further comprise steroidal or. The composition may further include steroidal or nonsteroidal antiphlogistics and/or antibiotics.

7 Claims, No Drawings

MEDICAMENTOUS FORM FOR USE AS AN OPHTHALMOLOGIC, OTOLARYNGOLOGIC, OR DERMATOLOGIC DRUG

BACKGROUND OF THE INVENTION

This invention relates generally to an antimicrobial form and more particularly to a medicamentous form for external use with a strong antiexudative, antiphlogistic, and antimicrobial effect in a suitable aqueous or ointment base applicable as an opthalmologic, otolaryngologic, or dermatologic drug.

Arachidic acid is liberated in damaged, wounded, or inflamed tissues from phospholipids of cytoplasmatic membranes by the action of phospholipase enzyme and may be then metabolized by the cyclooxygenase cycle (by cyclooxygenase enzyme) or the lipooxygenase cycle (by lipooxygenase enzyme) to prostanoids and eicosanoids. Antiphlogistics of both the steroid and nonsteroid nature, antibiotics, and sulfonamides are often used for therapeutic purposes. The antibiotics, which specifically suppress pathogenic microbes and are often used in ophthalmology, are tetracycline, chloramphenicol, bacitracin, and neomycin. Therapeutics which prevent the development of inflammation (antiphlogistics) are both steroid and nonsteroid. The steroid antiphlogistics (e.g., dexamethasone) block phospholipase. The antiinflammatory drugs of nonsteroid nature (e.g., indomethacin, flurbiprofen, pirprofen) block cyclooxygenase and others. The blockage of these enzymes is important, because the products formed in metabolic cycles have a strong chemotactic effect (they cause accumulation of leucocytes in the sites of origin), (e.g., some leucotrienes) and increase the vascular permeability. This contributes to an excess development of the inflammation. Inflammations, (both of infectious and noninfectious origin) are very dangerous for the anterior and posterior segments of the eye. Thus, scars formed in the cornea during the final stage of the healing process cause the loss of an exceptional function of this tissue, i.e. transparency. The loss of transparency of optical media of the eye (cornea, lens) then leads to a reduction or even loss of sight.

A disadvantage of locally applied antiphlogistics is the relatively low efficiency, retarded healing, and contribution to the development of infection. The local effect of antibiotics is limited. There is also a danger of development of an allergic reaction. A higher concentration of the antibiotics, which is necessary for obtaining the healing effect in many cases, acts toxically on the tissue. For this reason, local treatment is mostly supplemented with the general administration of antibiotics, which has disastrous consequences with respect to the suppression of antibody formation and the damage to the striking power of organism against infection. To this end, there have been several attempts to provide positive methods of treatment.

One of the very prospective possibilities of treatment is the inhibition of plasmin and other destruction proteases (e.g., collagenase or elastase) with specific inhibitors. These enzymes either directly develop the destruction processes (e.g., plasmin) or enable these processes by their own activity (e.g., collagenase, elastase). However, plasmin is effective not only as an initiator developing the degeneration processes proceeding in cascades, but also contributes to an excessive development of inflammation by several other mechanisms of which at least chemotaxis should be mentioned.

Apart from other methods, plasmin can be inhibited by aprotinin. This substance, when administered in an aqueous solution and low concentrations, has been successfully used in the treatment of some lesions of the anterior segment of the eye. Aprotinin inhibits not only plasmin but also several other proteolytic enzymes (for example, leucocytic elaslase), which contributes to the destruction processes.

What is needed then is a medicamentous form for external use as an opthalmologic, otolaryngologic, and dermatologic drug.

This medicamentous form must have strong antiexudative, antiphlogistic, and antimicrobial effect. This medicamentous form is presenting lacking in the prior art.

SUMMARY OF THE INVENTION

The medicamentous form or composition of the present invention is delivered in an aqueous or ointment base particularly suited for ophthalmologic, otolaryngologic, and dermatologic application. This medicamentous form contains inhibitors or proteases such as aprotinin, soybean inhibitor of trypsine, and elastatinal. These can also be delivered with antiphlogistics and antibiotics.

Accordingly, an object of the present invention is to provide a medicamentous form having strong antiexudative, antiphlogistic and antimicrobial effects.

Still another object of the present invention is to provide a medicamentous form having therapeutic effects including the inhibition of plasmin, leucolytic elastase, and other serine proteases.

Another object of the present invention is to provide a medicamentous form that inhibits the activation of latent forms of some endoproteases and several further subsequent reactions of chemotaxsis and vascularization of the cornea.

Yet another object of the present invention is to prevent the development of some diseases and stop the development of other diseases.

DETAILED DESCRIPTION OF THE PREFERRED EMBODIMENT

The composition of the present invention is a medicamentous form or composition in an aqueous or ointment base particularly suitable for opthalmologic, otolaryngologic, and dermatologic application. The medicamentous form contains inhibitors of proteases such as aprotinin, soybean inhibitor of trypsine, and elastatinal having a concentration of substantially 0.1 to 20 mg per 1 ml of solution or per 1 g. of ointment base. These inhibitors are applied either individually or in combination after being dissolved in physiological saline or buffer solution with a pH of 6.5 to 7.5, which is advantageously ionically balanced (e.g., phosphate or borax buffer) or present in the ointment base.

The ionically balanced buffer solution means that sodium chloride is added to the buffer solution in such a way that the 15 resulting solution is ionically balanced. For example, the precise performance for borax buffer with pH 7.4 is as follows:

Solution A—1.9 g. $Na_2P_4O_7$ per 100 ml $H_2O$ pro injectione

Solution B—1.25 g. $H_3BO_3$+0.3 g. NaCl per 100 ml $H_2O$ pro injectione

Provides a mix of—10 ml of solution A + 90 ml of solution B.

The medicamentous form according to the preferred embodiment in the liquid state may further advantageously contain 0.05 to 15 percent by weight of thickeners selected from the group comprising hydroxypropyl methyl cellulose, methyl cellulose, polyvinylpyrrolidone, polyvinyl alcohol, poly (alkylene glycols), poly/hydroxyalkyl, (meth)acrylates or poly(meth)acrylamides.

High concentrations of aprotinin, or another inhibitor, when locally applied, act not only curably in the advanced stage of disease but also prospectively by the prevention of the formation of destructive processes if timely administered. The vehicles or thickeners with protracted effect then enable a longer contact of the remedy (e.g., aprotinin) with the tissues.

The combination of aprotinin with other inhibitors, such as 10 elastatinal or inhibitors from soybeans, enhances the therapeutical effect.

The medicamentous form according to the preferred embodiment may contain 0.05 to 1.5 percent by weight of steroidal antiphlogistics such as indomethacin or 0.2 to 1 percent by weight of antibiotics such as bacitracin, neomycin, tetracycline, or chloramphenicol.

The combination of protease inhibitors with antiphlogistics or antibiotics, or all substances together, increases the antiinflammatory and anti-microbial effect because the inhibitors block some products of microbes such as elastase or other proteases. This enables one to use the antibiotics only locally and in smaller doses. The concentration of antiphlogistics may be reduced and, at the same time, the therapeutic effect is higher and the time of treatment shorter which is of great value in healing of tissue.

The medicamentous form is most often applied by instillation or as an ointment into the conjunctival sac. However, it can also be used for irrigation or lubrication of the eye, facial sinuses, and external auditory meatus. It may also be injected into the anterior eye chamber and other places. The medicamentous form in the liquid state may be also present in a hydrophilic three-dimensional polymer matrix in the form of a strip, contact lens, and the like from which the active components are released. The incorporation of medicamentous form into a hydrophilic matrix can be performed according to the invention by conditioning of the matrix in the solution of the medicamentous form in order to obtain the required concentration of inhibitors and also for the antiphlogistics and antibiotics in polymer matrix.

The invention is illustrated in the examples of performance and the examples are provided without the intention of limiting the scope of the present invention.

The preparation of medicamentous form in liquid state is begun by separately dissolving each substance in a small amount (10 to 40 ml) of buffer or physiological saline.

The ointment base is prepared by melting 10 g. lanolin, 10 g. liquid paraffin, and 80 g. white vaseline in bath water. The mixture is then strained through a hydrophilic gauze and sterilized. If the applicable therapeutic is easily soluble in water, it is dissolved in the necessary amount of distilled water for the preparation of injections, mixed with the ointment base in part melted in a water bath and stirred until completely cooled. If the therapeutic is insoluble in water, it is used for the preparation in the finest powdered form. However, it is first titrated in a smaller amount of liquid paraffin and then mixed with the ointment base.

EXAMPLE 5

A mixture is provided by combining aprotinin 0.01 g.; hydroxypropyl methyl cellulose 1 g.; and ionically balanced borax buffer of pH 7.4 up to 100 g. Drops of this composition dosed into the conjuctival sac of a patent at intervals of 3 hours healed allergic conjunctivitis within 3 to 5 days.

EXAMPLE 2

A mixture is provided by combining aprotinin 0.005 g.; hydroxypropyl methyl cellulose 2.5 g.; and ionically balanced phosphate buffer of pH 7.4 up to 100 g. The drops were dosed into the conjuctival sac of a patient three times a day. Noninfectious conjunctivitis was healed within a week.

EXAMPLE 3

A mixture was prepared by combining aproptinin 0.05 g.; polyvinylpyrrolidone (molecular weight 360,000) 1 g.; and ionically balanced phosphate buffer of pH 7.2 up to 100 g. The defects of corneal epithelium of a patient were healed within four days of administration of a drop into the conjunctival sac at intervals of every 4 hours.

EXAMPLE 4

A mixture was prepared by combining aprotinin 0.005 g.; polyvinylalcohol 1 g.; and ionically balanced borax buffer of pH 7.4 up to 100 g. Drops of the mixture were applied into the conjunctival sac of the patient at intervals of 2 hours. This healed minute wounds of the conjunctive, cornea, and eyelids within 2 to 4 days.

EXAMPLE 5

A mixture was prepared by combining aprotinin 0.2 g.; hydroxypropyl methyl cellulose 2.5 g.; and physiological saline up to 100 g. An etched and burnt cornea was healed during 4 days by application of the drops four times a day. The transparency of the cornea was recovered either completely or at least in the periphery of the cornea.

EXAMPLE 6

A mixture was prepared by combining aprotinin 0.002 g.; inhibitor from soybeans 2 g.; and ionically balanced borax buffer up to 100 g. The drops were dosed into the conjunctival sac at intervals of 2 hours. This was successful in achieving faster reepithelization after therapeutic abrasion of corneal epithelium.

EXAMPLE 7

A mixture was prepared combining aprotinin 0.025 g.; elastatinal 0.005 g.; hydroxypropyl methyl cellulose 2.5 g.; and ionically balanced borax buffer up to 100 g. The drops were applied into the conjunctival sac every 4 hours. This test was successfully used in the treatment of corneal infiltrates which disappeared within a week.

EXAMPLE 8

A mixture was prepared combining aprotinin 0.04 g.; inhibitor from soybeans 0.1 g.; hydroxypropyl methyl cellulose 2.5 g.; elastatinal 0.01 g.; and ionically balanced phosphate buffer up to 100 g. The drops were used for the treatment of a cornea etched with concentrated acids and hydroxides. The cornea healed within a month, and the transparency was recovered either completely or in part.

EXAMPLE 9

A mixture was prepared combining aprotinin 0.01 g.; deamethasone sodium phosphate 0.1 g.; hydroxypropyl methyl cellulose 2.5 g.; and ionically balanced borax buffer up to 100 g. The eye drops healed severe allergic conjunctivitis by instillation three times a day.

EXAMPLE 10

A mixture was prepared combining aprotinin 0.1 g.; deamethasone sodium phosphate 0.5 g.; hydroxypropyl methyl cellulose 2 g.; and ionically balanced phosphate buffer up to 100 g. The drops were administered into a conjunctival sac 3 times a day. The ulcers of the cornea of various origins healed during a week.

EXAMPLE 11

A mixture was prepared combining aprotinin 0.1 g.; elastatinal 0.01 g.; prednisolone acetate 0.02 g.; polyvinylpyrrolidone (molecular weight 360,000) 1 g.; and ionically balanced phosphate buffer of pH 7.4 up to 100 g. The drops were administered 4 times a day for treatment of deep corneal infiltrates. Healing occurred within a week. In the cases complicated with a secondary inflammation of the iris, the inflammation disappeared during a week.

EXAMPLE 12

A mixture was prepared combining aprotinin 0.05 g.; hydroxypropyl methyl cellulose 2.5 g.; and ionically balanced phosphate buffer (pH 7.4) up to 100 g. The drops were instilled 4 times a day. The symptoms of irritation of the eye after extraction of a cataract receded during several days.

EXAMPLE 13

A mixture was prepared combining aprotinin 0.1 g.; diclofenac 0.05 g.; hydroxypropyl methyl cellulose 3 g.; and ionically balanced borax buffer up to 100 g. The drops were administered into the conjunctival sac 4 times a day. This prevented the vascularization of the cornea caused by wearing hydrophilic contact lenses.

EXAMPLE 14

A mixture was prepared combining aprotinin 0.05 g.; flurbiprofen 0.1 g.; hydroxypropyl methyl cellulose 3 g.; and ionically balanced phosphate buffer of pH 7.2 up to 100 g. The drops were administered into the conjunctival sac in intervals of 4 hours. The defects of the corneal epithelium healed within several days. In other cases, the drops were successfully used for inhibition of the vascularization of cornea after application of contact lenses.

EXAMPLE 15

A mixture was prepared by combining aprotinin 1 g.; desamethasone sodium phosphate 0.1 g.; indomethacin 1 g.; and elastatinal 0.1 g. A contact lens of HEMA—DEGMA (the crosslinked copolymer of 2-hydroxyethyl methacrylate with ethylene glycol methacrylate containing 55 percent by weight of equilibrium water) was applied onto and eye etched with strong alkalies and the drops were administered over the contact lens at intervals of 4 hours. The lesion healed within 3 weeks.

EXAMPLE 16

A mixture was prepared by combining aprotinin 0.5 g.; neomycin sulfate 0.35 g.; hydroxypropyl methyl cellulose 2.5 g.; and ionically balanced phosphate buffer (pH 7.2) up to 100 g. The drops were applied at intervals of 3 hours at bacterial keratitis. The cornea afflicted by the infection of Pseudomonas aeruginosa healed during 5 days.

EXAMPLE 17

A mixture was prepared by combining aprotinin 0.75 g.; chloramphenicol 0.5; indomethacin 1 g.; hydroxypropyl methyl cellulose 3 g.; and ionically balanced borax buffer (pH 7.2) up to 100 g. The drops were applied 3 times a day for the treatment of nonhealing corneal ulcers. The cornea healed during a week.

EXAMPLE 18

A mixture was prepared by combining aprotinin 1 g.; tetracycline 0.3 g.; elastatinal 0.2 g.; flurbiprofen 0.5 g.; hydroxypropyl methyl cellulose 3 g.; and ionically balanced phosphate buffer (pH 7.4) up to 100 g. The drops were applied at intervals of 3 hours into eyes etched with concentrated hydroxides. The cornea did not break down and healed with a scar within a month.

EXAMPLE 19

A mixture was prepared by combining elastatinal 0.5 g.; dexamethasone sodium phosphate 0.1 g.; polyvinylalcohol 2 g.; and physiological saline up to 100 g. The drops were applied into a conjunctival sac at intervals of 3 hours. The perforation of the cornea healed during a week.

EXAMPLE 20

A mixture was prepared by combining elastatinal 0.3 g.; soybean inhibitor of trypsine 0.2 g.; hydroxypropyl methyl cellulose 2 g.; and ionically balanced phosphate buffer (pH 7.4) up to 100 g. The drops were applied into a conjunctival sac 4 times a day. The defects of the corneal epithelium healed within a week.

EXAMPLE 21

A mixture was prepared by combining aprotinin 0.1 g.; elastatinal 0.05 g.; dexamethasone sodium phosphate 0.1 g.; chloramphenicol 0.5 g. and physiological saline up to 100 g. The solution was successfully used in the treatment of rhinal allergoses and allergoses of meatus acusticus externus.

EXAMPLE 22

A mixture was prepared by combining aprotinin 0.25 g.; prednisolone acetate 0.025 g.; neomycin sulfate 0.015 g.; and ointment base up to 5 g. The ointment was applied into a conjunctival sac at intervals of 4 hours. Both were surfacial and deep corneal inflammations healed within a week. This ointment was very efficient in the treatment of an infected skin wound.

EXAMPLE 23

A mixture was prepared by combining elastatinal 0.1 g.; aprotinin 0.1 g.; dexamethasone sulfate 0.15 g.; flurbiprofen 0.1 g.; chloramphenicol; and physiological saline up to 100 g. A contact lens made from the crosslinked copolymer of 2-hydroxyethyl methacrylate and diethylene glycol methacrylate (HEMA - DEGMA) (55 percent by weight of equilibrium water content) was swelled in a solution for 24 hours. The contact lens was used for the treatment of a corneae burned with alkalies and lime. Healing and integrum occurred in some cases. In more severe cases, where the cornea usually had broken down, the tissue was healed after the application of the contact lens. In other cases, the contact lens proved very suitable for the treatment of corneal ulcers.

EXAMPLE 24

A mixture was prepared by combining aprotinin 1 g.; elastatinal 0.1 g.; flurbiprofen 0.1 g.; dexamethasone sodium phosphate 0.1 g.; neomycin sulfate; and physiological saline up to 100 g. A contact lens form the cross-linked polymer of 2-hydroxyethyl methacrylate (38 percent by weight of equilibrium water) was swelled in the given solution for 24 hours. The contact lens was used for the treatment of nonhealing corneal erosions. Within a week after application the reepithalization was sped up. Extraordinary results were attained after severe etching and burning of the anterior segment of the eye. The intraocular inflammation did not develop, the cornea did not exhibit ulceration and healed with a scar to place within a month. The transparency recovered in the periphery of the cornea.

EXAMPLE 25

A mixture was prepared by combining aprotinin 0.02 g.; elastatinal 0.05 g.; dexamethasone sulfate 0.1 g.; chloramphenicol 0.2 g.; and ionically balanced phosphate buffer (pH 7.4) up to 100 g. A strip of HEMA - DEGMA material (55 percent by weight of equilibrium water content) was immersed for 24 hours in a solution of the composition and then applied into the lower fornix of the eye. After 24 hours, the strip was removed from eye, immersed in the given solution overnight, and applied again. Corneal ulcers of various origins were healed after a week of treatment.

Thus, although there have been described particular embodiments to the present invention of a new and useful medicamentous form for external use as an ophthalmologic, otolaryngologic, or dermatologic drug, it is not intended that such references be construed as limitations upon the scope of this invention except to set forth in the following claims. Further, although there have been described certain parameters used in the preferred embodiment, it is not intended that such parameters be construed as limitations upon the scope of this invention except as set forth in the following claims.

We claim:

1. A medicinal composition for external use with an antiexudation, antiphlogistic, and antimicrobial effect, comprising an aqueous or ointment base containing an inhibitor of proteases selected from the group consisting of elastatinal alone, and elastatinal plus at least one of aprotinin, and soyabean trysine inhibitor, and mixtures thereof, with a concentration of from 0.1 to 20 mg of inhibitor of proteases per 1 ml of aqueous base selected from the group consisting of pharmaceutical saline or buffer solution, or per 1 g of ointment base.

2. The composition of claim 1 further comprising at least one antiphlogistic.

3. The combination of claim 2 wherein said antiphlogistic is selected from the group consisting of substantially 0.05 to 1.5 percent by weight of steroidal antiphlogistics such as dexamethasone, and 0.05 to 5 percent by weight of non-steroidal antiphlogistics such as indomethacin.

4. The composition of claim 1 further comprising substantially 0.2 to 1 percent by weight of an antibiotic.

5. The composition of claim 4 wherein said antibiotic is selected from the group consisting of neomycin, bacitracin, chloramphenicol, and tetracycline.

6. The composition of claim 2 further comprising 0.05 to 15 percent by weight of thickeners.

7. The composition of claim 6 wherein said thickener is selected from the group consisting of hydroxypropyl methyl cellulose, methyl cellulose, polyvinylpyrrolidone, polyvinylalcohol, poly (alkylene glycols), poly [alkylene glycol (meth) acrylates], and poly (meth) acrylamides.

* * * * *